(12) United States Patent
Fein et al.

(10) Patent No.: US 11,801,275 B2
(45) Date of Patent: Oct. 31, 2023

(54) COMPOSITIONS AND METHODS FOR COMMON COLDS

(71) Applicant: M. ALPHABET 3, LLC, Delray Beach, FL (US)

(72) Inventors: Howard Fein, Redondo Beach, CA (US); Joshua M. Berlin, Boca Raton, FL (US)

(73) Assignee: M. ALPHABET 3, LLC, Delray Beach, FL (US)

(*) Notice: Subject to any disclaimer, the term of this patent is extended or adjusted under 35 U.S.C. 154(b) by 766 days.

(21) Appl. No.: 16/478,554

(22) PCT Filed: Jan. 17, 2018

(86) PCT No.: PCT/US2018/014011
§ 371 (c)(1),
(2) Date: Jul. 17, 2019

(87) PCT Pub. No.: WO2018/136490
PCT Pub. Date: Jul. 26, 2018

(65) Prior Publication Data
US 2019/0328802 A1 Oct. 31, 2019

Related U.S. Application Data

(60) Provisional application No. 62/447,389, filed on Jan. 17, 2017.

(51) Int. Cl.
| | |
|---|---|
| *C12N 1/20* | (2006.01) |
| *A61K 35/747* | (2015.01) |
| *A61P 39/00* | (2006.01) |
| *A61K 31/366* | (2006.01) |
| *A61K 31/375* | (2006.01) |
| *A61K 31/59* | (2006.01) |
| *A61K 31/592* | (2006.01) |
| *A61K 31/593* | (2006.01) |
| *A61K 31/7048* | (2006.01) |
| *A61K 33/06* | (2006.01) |
| *A61K 35/745* | (2015.01) |
| *A61K 36/185* | (2006.01) |
| *A61K 36/738* | (2006.01) |
| *A61K 45/06* | (2006.01) |

(52) U.S. Cl.
CPC .......... *A61K 35/747* (2013.01); *A61K 31/366* (2013.01); *A61K 31/375* (2013.01); *A61K 31/59* (2013.01); *A61K 31/592* (2013.01); *A61K 31/593* (2013.01); *A61K 31/7048* (2013.01); *A61K 33/06* (2013.01); *A61K 35/745* (2013.01); *A61K 36/185* (2013.01); *A61K 36/738* (2013.01); *A61K 45/06* (2013.01); *A61P 39/00* (2018.01)

(58) Field of Classification Search
CPC ...................................................... C12N 1/20
See application file for complete search history.

(56) References Cited

U.S. PATENT DOCUMENTS

| | | | |
|---|---|---|---|
| 2009/0230013 A1* | 9/2009 | Born | ............... A61J 7/0084 206/534 |
| 2015/0320809 A1 | 11/2015 | Carpenter et al. | |
| 2016/0129058 A1 | 5/2016 | Chang et al. | |
| 2016/0192689 A1 | 7/2016 | Horn | |

OTHER PUBLICATIONS

International Search Report in International Patent Application No. PCT/US18/14011, dated Mar. 8, 2018, in 2 pages.
Gleeson, M. et al, Effects of a Lactobacillus salivarius probiotic intervention on infection, cold symptom duration and severity, and mucosal immunity in endurance athletes. International Journal of Sport Nutrition and Exercise Metabolism, 2012, 22 (4), pp. 235-242.
Tapiovaara, L. et al., Human rhino virus in experimental infection after peroral Lactobacillus rhamnosus GG consumption, a pilot study. Int Forum Allergy Rhinol. 2016, 6(8), 848-853.
Kumpu, M. et al. Effect of live and inactivated Lactobacillus rhamnosus GG on experimentally induced rhinovirus colds: randomised, double blind, placebo-controlled pilot trial, Beneficial Microbes: 2015, 6 (5)—pp. 631-639; https://doi.org/10.3920/BM2014.0164.
Hemilä H., Chalker E. Vitamin C for preventing and treating the common cold. Cochrane Database Syst Rev. Jan. 31, 2013;(1) Published by John Wiley & Sons, Ltd., 105 pages; Art. No.: CD000980. DOI: 10.1002/14651858.CD000980.pub4.
Murdoch, David R., et al. "Effect of vitamin D3 supplementation on upper respiratory tract infections in healthy adults: the VIDARIS randomized controlled trial." JAMA 308.13 (2012): 1333-1339.
Garaiova, I., et al. "Probiotics and vitamin C for the prevention of respiratory tract infections in children attending preschool: a randomised controlled pilot study." European journal of clinical nutrition 69.3 (2015): 373-379.

* cited by examiner

*Primary Examiner* — Rosanne Kosson
(74) *Attorney, Agent, or Firm* — DUANE MORRIS LLP

(57) ABSTRACT

This disclosure relates to pharmaceutical compositions for preventing, treating, reducing the duration, or reducing the severity of symptoms of the common cold. The pharmaceutical composition can comprise a probiotic formulation of non-pathogenic bacteria, vitamin C and vitamin D along with a pharmaceutically acceptable excipient or filler. A method of for preventing, treating, reducing the duration, or reducing the severity of symptoms of the common cold is also disclosed in which a patient in need of a treatment for preventing, treating, reducing the duration, or reducing the severity of symptoms of the common cold is identified. The pharmaceutical composition can then be administered orally to the patient.

20 Claims, No Drawings

COMPOSITIONS AND METHODS FOR COMMON COLDS

RELATED APPLICATION

This Application claims priority to U.S. Prov. Pat. App. No. 62/447,389, filed Jan. 17, 2017, and PCT/US2018/014011, filed Jul. 17, 2019, each of which is herein incorporated by reference in its entirety for all purposes.

FIELD OF THE INVENTION

The present invention relates to compositions and methods of preventing or treating upper respiratory tract ailments, and more particularly, to compositions comprising probiotic bacteria, Ester-C®, calcium ascorbate, and a vitamin D, and methods for preventing, treating, reducing the duration, or reducing the severity of symptoms of the common cold.

BACKGROUND

The common cold (also known as nasopharyngitis, rhinopharyngitis, acute coryza, head cold, or simply a cold) is a contagious viral infection of the upper respiratory tract, which includes the tissues lining the nose and throat. More than 200 different viral strains are implicated in causing the common cold. The rhinovirus, a type of picornavirus, which accounts for about 30%-80% of all colds is the most common cause. The rhinovirus itself has 99 known serotypes. Other agents that cause common cold include human coronavirus (causing about 15% of all colds), influenza viruses (10-15%), adenoviruses (5%), human respiratory syncytial virus, other enterovirus, human parainfluenza virus, and metapneumovirus. Frequently more than one virus is present and secondary bacterial infections are quite common.

The common cold virus is typically transmitted via airborne droplets (aerosols), direct contact with infected nasal secretions, or fomites (contaminated objects). Which of these routes is of primary importance has not been determined; however, hand-to-hand and hand-to-surface-to-hand contact seems of more importance than transmission via aerosols.

A cold usually begins with fatigue, a feeling of being chilled, sneezing, and a headache, followed in a couple of days by a runny nose and cough. Symptoms may begin within sixteen hours of exposure and typically peak two to four days after onset. They usually resolve in seven to ten days but some can last for up to three weeks.

Signs and symptoms of common cold, which are primarily due to the body's immune response to the infection rather than to tissue destruction by the viruses themselves, include coughing, sore throat, runny nose, sneezing, and fever. The symptoms usually resolve in seven to ten days, however in some cases can last several weeks or even longer. The mechanism of this immune response is virus specific. For example, the rhinovirus is typically acquired by direct contact; it binds to human ICAM-1 receptors through unknown mechanisms to trigger the release of inflammatory mediators. These inflammatory mediators then produce the symptoms. It does not generally cause damage to the nasal epithelium.

SUMMARY

The current invention is based, in part, on observation that pharmaceutical compositions described herein are effective in preventing, treating, reducing the duration, or reducing the severity of symptoms of the common cold. The pharmaceutical composition can include active agents described below along with a pharmaceutically acceptable excipient or filler.

In one aspect, the current invention method of preventing, treating, reducing the duration, or reducing the severity of symptoms of the common cold, comprising administration of a composition comprising a probiotic formulation of non-pathogenic bacteria, a vitamin C and a vitamin D.

In some embodiments, a method for preventing, treating, reducing the duration, or reducing the severity of symptoms of the common cold comprises administration of the composition by at least one of the following routes: orally into the digestive tract; orally buccal, sublingual or sublabial; orally by inhalation into the respiratory tract; ocularly, nasally, through the urogenital tract intravesicularly or intravaginally; rectally, or topically. In some embodiments, the compositions described herein may be delivered by oral, inhaled or intranasal administration.

In some embodiments, the compositions described herein contain about 1 mg to about 2000 mg of vitamin C. In some embodiments the vitamin C component may comprise vitamin C metabolites. In some embodiments, the vitamin C component may be calcium ascorbate, and may further comprise vitamin C metabolites. In some embodiments vitamin C is provided in the form of Ester-C®, comprising vitamin C metabolites and calcium ascorbate. In some embodiments the vitamin C metabolites in Ester-C® may be, for example, vitamin C metabolites in the form of 1-5% calcium threonate, 1-3% calcium threonate, or 1, 2, 3, 4, 5, 6, 7, 8, 9 or 10% calcium threonate in addition to the calcium ascorbate. In some embodiments, the formulations of this invention comprising a vitamin C component comprising calcium ascorbate and vitamin C metabolites, e.g., Ester-C®, the vitamin C/metabolite mixture increases intracellular uptake into leukocytes and enhances the leukocyte viral killing effect.

In some embodiments, the formulation excludes vitamin C in the form of ascorbic acid. Providing vitamin C in the form of a salt such as calcium ascorbate or an ester such as ascorbyl palmitate neutralizes or reduces the acidic effect of the Vitamin C, enhancing tolerability of the formulation and prolonging the survival of the probiotic components.

In some embodiments the formulation may include or exclude Vitamin D2 or analgesics, anticholinergics, antihistamines, anti-inflammatories, antipyretics, antitussives, antivirals, decongestants, expectorants, mucolytics, and combinations thereof.

In some embodiments the vitamin C consists essentially of calcium ascorbate and vitamin C metabolites. In such embodiments, the basic function of the calcium ascorbate/vitamin C metabolite is to enhance leukocyte concentrations of ascorbate. In some embodiments, the amount of vitamin C, e.g., Ester-C®, or other composition comprising calcium ascorbate and vitamin C metabolites, present in the adult dose of compositions described herein may be between about 200 to about 1500 mg, from 50, 75, 100, 125, 150, 175, 200, 225, 250, 275, 300, 325, 350, 375, 400, 425, 450, 475, 500, 600, 700,800, 900, 1000, 1100, 1200, 1300, 1400, 1500, 1600, 1700, 1800, 1900, 2000 mg, or any amount or range of amounts between any two of the recited amounts. In some embodiments, the amount of vitamin C e.g., Ester-C®, or other composition comprising calcium ascorbate and vitamin C metabolites, present in the pediatric dose of compositions described herein may be between about 25 to about 500 mg, from 50-500 mg, from 75-500 mg, from 75-400 mg, 75-300 mg, 75-200 mg, 75-100 mg, 25, 50, 75, 100, 125, 150, 175, 200, 225, 250, 275, 300, 325, 350, 375, 400, 425, 450, 475, 500, 600, 700,800, 900, 1000, 1100, 1200, 1300, 1400, 1500, 1600, 1700, 1800, 1900, 2000 mg, or any amount or range of amounts between any two of the recited amounts.

In some embodiments, the formulations of this disclosure further comprise Vitamin C absorption cofactors, for example, citrus bioflavonoids, acerola, rose hips, and rutin, to further enhance uptake of vitamin C and/or its metabolites.

In some embodiments, the vitamin C, e.g, Ester-C®, present in the compositions of current compositions is ascorbic acid or an ester thereof. In some embodiments, the vitamin C present in the compositions described herein is selected from the group consisting of Ester-C®, a mixture of calcium ascorbate and vitamin C metabolites such as calcium threonate, sodium ascorbate, calcium ascorbate, potassium ascorbate, magnesium diascorbate, ascorbyl palmitate, and ascorbyl stearate. In some embodiments, the form of vitamin C present in the compositions described herein is an ester of vitamin C, which includes but is not limited to, ascorbyl laurate, ascorbyl myristate, ascorbyl palmitate, ascorbyl stearate, ascorbyl dilaurate, ascorbyl dimyristate, ascorbyl dipalmitate, ascorbyl distearate, ascorbyl trilaurate, ascorbyl trimyristate, ascorbyl tripalmitate, ascorbyl tristearate, ascorbyl tetralaurate, ascorbyl tetramyristate ascorbyl tetrapalmitate, ascorbyl tetrastearate, and mixtures thereof.

In some embodiments, the compositions described herein contain about 1 IU to about 200,000 IU of vitamin D, for example vitamin D3. In some embodiments, the amount of vitamin D, e.g., vitamin D3 present in an adult dose of compositions is between from about 100 IU to about 5000 IU. In some embodiments, the amount of vitamin D, e.g., vitamin D3 is from about 400 IU to about 1200 IU. In some embodiments, the amount of vitamin D, e.g., vitamin D3 is present in an adult dose is from about 100 IU to about 2000 IU, from 200 IU to 1500 IU or from 400 IU to 1200 IU. In some embodiments, the amount of vitamin D, e.g., vitamin D3 is present in a pediatric dose is from about 50 IU to about 2000 IU, from 150 IU to 1500 IU, or from 300 IU to 1200 IU.

In some embodiments, the vitamin D present in the compositions of current compositions is in the form vitamin D1, vitamin D2, vitamin D3, vitamin D4, vitamin D5 or a mixture thereof, or a hydroxy derivative thereof. In some embodiments, the vitamin D is 1,25-dihydroxy vitamin D3. In some embodiments, the compositions of this disclosure may exclude vitamin D2.

In some embodiments, the compositions described herein contain about 1 billion to about 500 billion colony forming units (CFU) of probiotic bacteria. In some embodiments, the composition contains from about from about 25 billion to about 51 billion colony forming units (CFU) of probiotic bacteria. In some embodiments, the amount of probiotic bacteria is present in an adult dose is from about 5 billion to about 100 billion CFU, from about 10 billion to about 80 billion CFU or from about 25 billion to about 51 billion CFU. In some embodiments, the amount of probiotic bacteria is present in a pediatric dose is from about 2 billion to about 100 billion CFU, from about 5 billion to about 50 billion CFU, or from about 10 billion to about 30 billion CFU.

In some embodiments, the compositions described herein comprises one or more probiotic bacteria selected from the group consisting of *Lactobacillus, Bifidobacterium, Strepetococcus, Pediococcus, Oenococcus, Leuconostoc, Saccharomyces, Enterococcus, Bacillus, Escherichia coli.* In some embodiments, the composition comprises one or more probiotic bacteria selected from the group consisting of *Bifidobacterium lactis, Lactobaccillus acidophilu, Bifidobacterium breve, Bifidobacterium longum, Lactobacillus casei, Lactobacillus plantarum, Lactobacillus arginine, Lactobacillus paracasei, Lactobacillus rhamnosus, Lactobacillus bulgaricus, Saccharomyces boulardii,* and *E. coli* Nissle 1917. In some embodiments, the composition comprises about 25 billion CFU of *Bifidobacterium lactis*, about *Lactobaccillus acidophilus* 15 billion CFU, about 2.5 billion CFU of *Bifidobacterium breve*, about 2.5 billion CFU of *Bifidobacterium longum*, about 1.50 billion CFU of *Lactobacillus casei*, about 1 billion CFU of *Lactobacillus plantarum*, about 1 billion CFU of *Lactobacillus arginine*, about 1 billion CFU of *Lactobacillus paracasei*, about 500 million CFU of *Lactobacillus rhamnosus* and about 500 million CFU of *Lactobacillus bulgaricus*. In some embodiments, the compositions of this disclosure excludes one or more of the following strains: *Lactobacillus acidophilus* CUL21 (NCIMB 30156), *Lactobacillus acidophilus* CUL60 (NCIMB 30157), *Bifidobacterium bifidum* CUL20 (NCIMB 30153) and/or *Bifidobacterium animalis* subsp. *lactis* CUL34 (NCIMB 30172.

In some embodiments, the composition is administered one to eight times a day. In some embodiments, the composition is administered once, twice, thrice, or four times a day.

In some embodiments, the composition is formulated as a unit dose formulation. In some embodiments, the composition the composition is formulated as a tablet, capsule, troches, lozenges, pellets, liquid, serum, yogurt, tea, drink, drops or aerosol, or a combination thereof. In some embodiments, the composition is enterically coated.

In some embodiments, the composition further comprises one or more agents selected from a prebiotic, a herbal extract, an antibiotic, a decongestant, an antihistamine, an analgesic, a cough suppressant, an expectorant, mineral, and a further vitamin. In some embodiments, the composition comprises one or more solvents, diluents, or other liquid vehicle, dispersion or suspension aids, surface active agents, isotonic agents, thickening or emulsifying agents, preservatives, solid binders, lubricants or mixtures thereof. In some embodiments, the composition described herein further comprises a binder, a humectant, a disintegrating agent, an absorption accelerator, a wetting agent, an absorbent or a lubricant.

In some aspects, this application describes use of a composition in the preparation of a medicament for preventing, treating, reducing the duration, or reducing the severity of symptoms of the common cold, wherein the composition comprises probiotic formulation of non-pathogenic bacteria, a vitamin C and a vitamin D.

Additional features and advantages are described herein, and will be apparent from, the following Detailed Description.

DETAILED DESCRIPTION

Common cold is the most frequent infectious disease in humans with the average adult getting two to three colds a year and the average child getting between six and twelve. It is a viral infection caused by about 200 different strains of viruses including rhinovirus, human coronavirus, influenza viruses, adenoviruses, human respiratory syncytial virus, other enterovirus, human parainfluenza virus, metapneumovirus, etc. The primary site of infection is in the nasal epithelium when caused by inhalation of airborne droplets (aerosols), direct contact with infected nasal secretions, or contaminated objects from infected individual. These viruses gain entry into nasal epithelium of the respiratory tract by binding to specific receptors present in the attack respiratory tract by binding to specific receptors. For example, human rhinoviruses bind ICAM-1 or CDHR3 receptors; coronaviruses use membrane ectopeptidases DPP4, ACE2 or APN; and human influenza viruses and parainfluenza viruses attach to sialic acid, a small sugar, present on many different proteins.

Upon gaining entry in cells, the actual mechanism of infection differs depending on the virus causing infection. However, all of these viruses trigger the inflammatory responses, which lead to the observed symptoms. For example, rhinorrhea (runny nose) and nasal obstruction are caused by increased vascular permeability and stimulation of mucus hypersecretion. Cough is probably caused by irritation from posterior pharyngeal drainage or direct infection of the large airways.

Symptoms include sore throat, runny nose, nasal congestion, malaise, sneezing, sinusitis and cough; sometimes accompanied by muscle aches, fatigue, malaise, headache, muscle weakness, or loss of appetite. Fever and extreme exhaustion are more usual in influenza. Children may have six to twelve colds a year. In the United States, the incidence of colds is higher in the autumn and winter, with most infections occurring between September to April. The seasonality may be due to the start of the school year and to people spending more time indoors (thus in proximity with each other), thereby increasing the chance of transmission of the virus. Lower ambient, especially outdoor, temperatures may also be factor given that rhinoviruses preferentially replicate at 32° C. (89° F.) as opposed to 37° C. (98° F.).

Although complications of varying degree are observed, common cold is generally mild and self-limiting with most symptoms generally improving in a week. Half of cases go away in ten days and 90% in fifteen days. Severe complications are usually in the very old, the very young, or those who are immunosuppressed. For example, patients suffering from asthma or other underlying chronic lung disease may suffer from lower respiratory tract infection causing cough, shortness of breath, chest tightness, and wheezing. The inflammation associated with obstruction of sinus openings and secondary Eustachian tube dysfunction can predispose to acute bacterial sinusitis and otitis media, respectively. Infections caused by human coronavirus, influenza viruses, parainfluenza viruses, etc., such as bronchitis and pneumonia, and associated bacterial infections can be severe or even fetal. Secondary bacterial infections may occur resulting in sinusitis, pharyngitis, or an ear infection. It is estimated that sinusitis occurs in 8% and an ear infection in 30% of cases.

No medications or herbal remedies have been conclusively demonstrated to shorten the duration of infection. Antibiotics are ineffective against viral infections and thus have no effect against the viruses that cause the common cold. Currently, there are no effective antiviral drugs for the common cold even though some preliminary research has shown benefits.

Treatment is primarily based on reducing the severity of symptoms. No current for the common cold exists, but the symptoms can be treated. For example, treatments that help with symptoms include analgesics and antipyretics, antihistaminics, nasal decongestants reduce severity of the symptoms. Similarly, getting plenty of rest, drinking fluids to maintain hydration, and gargling with warm salt water, are reasonable conservative measures. However much of the benefit from treatment is attributed to the placebo effect.

While there are many alternative treatments used for the common cold such as the herbs and homeopathic products, there is insufficient scientific evidence to support their use. Zinc has been used to treat symptoms, with studies suggesting that zinc, if taken within 24 hours of the onset of symptoms, reduces the duration and severity of the common cold in otherwise healthy people. Due to wide differences between the studies, further research may be needed to determine how and when zinc may be effective. Whereas the zinc lozenges may produce side effects, there is only a weak rationale for physicians to recommend zinc for the treatment of the common cold. Some zinc remedies directly applied to the inside of the nose have led to the loss of the sense of smell. Although there have been extensive studies, there is no credible evidence that the widely promoted herbs Echinacea or Golden Seal provide any meaningful benefit in treating or preventing colds.

The economic impact of the common cold is not well understood in much of the world. In the United States, the common cold leads to 75-100 million physician visits annually at a conservative cost estimate of $7.7 billion per year. Americans spend $2.9 billion on over-the-counter drugs and another $400 million on prescription medicines for symptomatic relief. An estimated 22-189 million school days are missed annually due to a cold. As a result, parents missed 126 million workdays to stay home to care for their children. When added to the 150 million workdays missed by employees suffering from a cold, the total economic impact of cold-related work loss exceeds $20 billion per year. This accounts for 40% of time lost from work in the United States.

The current inventor surprisingly discovered that a combination a probiotic formulation of non-pathogenic bacteria, a vitamin C and a vitamin D is efficacious for prevention and treatment of common cold. Accordingly, this featured is a method for the treatment and/or prevention of the common cold, a self-limited viral infection of the upper respiratory tract. The method involves the daily administration of an oral preparation containing a (1) probiotic formulation of non-pathogenic bacteria, (2) Vitamin C (ascorbic acid or ester thereof), and (3) Vitamin D (1,25 dihydroxyvitamin D). The preparation can be taken daily for cold prophylaxis before symptoms are present or before exposure to the cold virus has occurred. For instance the preparation can be taken daily during peak cold season which runs from August through March. Alternatively, the preparation can be taken on-demand as a treatment to reduce either the duration and/or severity of symptoms once the cold virus infection has begun; in the setting of acute cold virus infection the preparation should be taken as soon as symptoms develop.

Probiotics are a preparation (a dietary supplement) containing live bacteria (such as *Lactobacilli*) that is taken orally to restore beneficial bacteria to the body. The World Health Organization (WHO) and the Food and Agriculture Organization of the United Nations (FAO) define probiotics as "live microorganisms that, when administered in adequate amounts as part of food, confer beneficial effects to the host through his intestinal flora." Recent in vivo and in vitro studies have demonstrated that various probiotic preparations containing either *Lactobacilli* and/or *Bifidobacterium* exert various beneficial immune enhancing effects. In particular, probiotic bacteria have been shown to enhance the production of immune stimulating cytokines such as interleukin 12 and interleukin 18. Both of these interleukins have previously been shown to be important in the body's natural response to viral infection. Probiotic bacteria have also been shown to enhance the activity of the body's innate immune system, which is important in controlling viral infections. Finally, probiotic bacteria are hypothesized to compete with potential viral pathogens for binding sites along the respiratory mucosa. Despite the abundance of promising findings as a potential anti-viral treatment, in vivo human studies with oral probiotic preparations as a potential treatment or prophylaxis for the common cold have been disappointing. In fact, several meta-analysis studies have been found these preparations to be ineffective.

In the recent years, there have a been a number of claims of utility of probiotics, also known as "good" and "beneficial" microbe, for preventing or treating common cold. However, that claim has also not found sufficient scientific basis. For example, Gleeson et al. (International Journal of Sport Nutrition and Exercise Metabolism 22: 235, 2012) reported that severity and duration of symptoms were not significantly different between human groups treated with placebo or probiotic *Lactobacillus salivarius*. Tapiovaara et al (Int Forum Allergy Rhinol. 6: 848, 2016) similarly showed no statistical differences in viral loads in subjects using *L. rhamnosus* GG when compared to placebo. In addition, Kempu et al., (Benef Microbes. 6:631, 2015) reported results of a preclinical study to assess efficacy of treatment with the probiotic *Lactobacillus rhamnosus* for preventing the common cold, and those results showed that differences between the treated and control group were not statistically significant, even though the reported occurrence and severity of cold symptoms was lower in the group receiving live *L. rhamnosus*. Thus, there are no reliable reports showing statistically significant protection offered by probiotics against the common cold.

Vitamin C is an important antioxidant that protects the body against the effects of reactive oxygen species that are generated by the immune system during the process of pathogen killing. In addition, vitamin C has also been shown to enhance the function and increase the production of various components of the immune system including lymphocytes, neutrophils, and phagocytes. Despite these findings, clinical trials examining the effects of oral vitamin C for either treatment or prophylaxis of the common cold have been unsuccessful. Several meta-analysis studies have shown vitamin C supplementation to be ineffective at treating and/or preventing infection with the common cold.

Vitamin C has also been widely advocated as a treatment for the common cold for about 70 years. However, extensive research with vitamin C has been disappointing, except in limited circumstances. Hemila and Chalker (Cochrane Database Syst Rev., 2013) compared twenty-nine placebo-controlled randomised, double-blind trials involving 11,306 participants to calculate risk ratio (RR) of developing a cold whilst taking vitamin C regularly over the study period. They found that the pooled RR was 0.97 (95% confidence interval (CI) 0.94 to 1.00) in the general community trials involving 10,708 participants. In contrast, five trials involving a total of 598 marathon runners, skiers and soldiers on subarctic exercises yielded a pooled RR of 0.48 (95% CI 0.35 to 0.64). Hemila and Chalker further found no consistent effect of vitamin C on the duration or severity of colds in the therapeutic trials. Therefore, vitamin C may to provide some benefit in people under physical stress (e.g., marathon runners or soldiers in subarctic environments), but no meaningful benefit has been shown for the average patient. Hemila and Chalker concluded that vitamin C supplementation failed to reduce the incidence of colds in the general population, and routine vitamin C supplementation is not justified. Vitamin C may be useful for people exposed to brief periods of severe physical exercise. Some trials involving regular supplementation of vitamin C showed reduction in the duration of colds, but this result was not replicated in other clinical trials.

Vitamin D also plays a role in both innate and adaptive immune responses. Vitamin D (1,25-dihydroxyvitamin D) exerts its effects through the vitamin D receptor (VDR) and is a potent stimulator of the immune system. The VDR is expressed by most cells of the immune system, including T cells, antigen-presenting cells, and macrophages. In addition, vitamin D induces cathelicidins, a group of antimicrobial peptides produced by neutrophils, macrophages, and epithelial cells. There is also considerable scientific evidence that 1,25-dihydroxyvitamin D plays a role in the immune system's response to viral infection. In addition, the natural wintertime deficiency of vitamin D, caused by decreased exposure to sunlight, is associated with the seasonal increase in colds and flu. Further, epidemiological studies show an association between low vitamin D levels and a variety of respiratory tract infections. For example, vitamin D insufficiency is associated with increased risk of developing tuberculosis.

Despite these findings, a recent clinical study failed to find any benefit for oral vitamin D at either preventing or reducing the duration of the common cold infection. Murdoch et al. (JAMA 30, 1333, 2012) reported results of a randomized, double-blind, placebo-controlled trial conducted among 322 healthy adults. Participants were given an initial dose of 200,000 IU oral vitamin D3 (or placebo) for a month, followed by 200,000 IU per day (or placebo) for another month, and then 100,000 IU of oral vitamin $D_3$ (or placebo) for rest of the study duration. Although the mean level of 25-hydroxy vitamin D increased from 29 (SD, 9) ng/mL to greater than 48 ng/mL, and was maintained at the higher level throughout the study, there was no statistically significant difference in upper respiratory tract infections, number of days of missed work as a result of an infection, duration of symptoms per episode, severity of symptoms, irrespective of season of measurement of infections.

Therefore, studies have shown that when used independently, probiotic bacteria, vitamin C, and vitamin D have all been proven to be ineffective at preventing, reducing the duration, or reducing the severity of symptoms of the common cold. Despite these limitations when used individually, this patent describes a synergistic, combination that can be used to prevent, reduce the duration, or reduce the severity of symptoms of common cold infection.

Garaiova et al. (European Journal of Clinical Nutrition 69: 373, 2015) have reported a small study of the effect of a combination $1.25 \times 10^{10}$ colony-forming units of *Lactobacillus acidophilus* CUL21 (NCIMB 30156), *Lactobacillus acidophilus* CUL60 (NCIMB 30157), and 50 mg of vitamin C (ascorbic acid) in young children in Slovakia. Although this study reported some efficacy, it is not clear whether this trend will survive a larger statistical scrutiny. Whether these results are relevant to other settings, for example to adult, elderly, school children, toddlers, in the U.S. and around the globe remains to be seen.

Unlike the Garaiova study, the instant invention requires vitamin D as an essential component. Unlike the Garaiova study, which used 50 mg of ascorbic acid, the preferred embodiment of the current invention requires Ester-C®, a buffered calcium salt of ascorbic acid and vitamin C metabolites. Further, Gariova reference disclosed a probiotic containing only two bacterial strains and a total dose of 1.5 billion CFU per day. In contrast, the preferred embodiment of the dose of instant invention for adults contains about 50 billion CFU and the preferred embodiment of the pediatric dose contains 5-10 billion CFU daily. In addition, Garaiova used only two strains of *Lactobacillus acidophilus* and two strains of *Bifidobacterium* (*B. bifidum* and *B. animalis*). In contrast the current invention requires a different blend of probiotics as described below. The preferred embodiment requires seven strains of lactobacilli and three strains of *Bifidobacterium*.

In one aspect, the methods of this disclosure include methods of preventing, treating, reducing the duration, or reducing the severity of symptoms of the common cold, the method comprising administering a composition comprising a probiotic formulation of non-pathogenic bacteria, a vitamin C and a vitamin D. The preparation can be taken daily for cold prophylaxis before symptoms are present or before exposure to the cold virus has occurred. For instance, the preparation can be taken daily during peak cold season which runs from August through March. Alternatively, the preparation can be taken on-demand as a treatment to reduce either the duration and/or severity of symptoms once the cold virus infection has begun; in the setting of acute cold virus infection the preparation should be taken as soon as symptoms develop.

In some embodiments, a method for preventing, treating, reducing the duration, or reducing the severity of symptoms of the common cold comprises administering the composition by at least one of the following routes: orally into the digestive tract; orally buccal, sublingual or sublabial; orally by inhalation into the respiratory tract; ocularly, nasally, through the urogenital tract intravesicularly or intravaginally; rectally, or topically. In some embodiments, the compositions described herein may be delivered by oral, inhaled or intranasal administration.

In some embodiments, the compositions described herein contain about 1 mg to about 2000 mg of vitamin C. In some embodiments the vitamin C is Ester-C®, or another composition comprising calcium ascorbate and vitamin C metabolites. In some embodiments, the amount of vitamin C present in the adult dose of compositions described herein may be between about 200 to about 1500 mg. In some embodiments, the amount of vitamin C present in an adult dose can be about 1 mg to about 55 mg, about 10 mg to about 100 mg, about 100 mg to about 200 mg, about 150 mg to about 250 mg, about 200 mg to about 400 mg, about 200 mg to about 500 mg, about 250 mg to about 750 mg, about 300 mg to about 900 mg, about 400 mg to about 1,000 mg, about 500 mg to about 1,200 mg, about 750 mg to about 1,400 mg, about 1,000 mg to about 1,500 mg, or about 600 mg to about 2,000 mg. In some embodiments, the amount of vitamin C present in an adult dose can be about 1 mg, about 5 mg, about 25 mg, about 50 mg, about 100 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,050 mg, about 1,100 mg, about 1,150 mg, about 1,200 mg, about 1,300 mg, about 1,400 mg, about 1,500 mg, about 1,600 mg, about 1,750 mg, about 2,000 mg, or any range of doses between any two of those doses. In some embodiments, the amount of vitamin C present in the pediatric dose of compositions described herein may be between about 25 to about 500 mg. In some embodiments, the amount of vitamin C present in a pediatric dose can be about 1 mg to about 50 mg, about 10 mg to about 50 mg, about 50 mg to about 100 mg, about 75 mg to about 125 mg, about 100 mg to about 200 mg, about 100 mg to about 250 mg, about 125 mg to about 400 mg, about 150 mg to about 500 mg, about 200 mg to about 500 mg, about 250 mg to about 600 mg, about 300 mg to about 800 mg, about 500 mg to about 800 mg, or about 300 mg to about 1,000 mg. In some embodiments, the amount of vitamin C present in a pediatric dose can be about 1 mg, about 5 mg, about 25 mg, about 30 mg, about 35 mg, about 40 mg, about 50 mg, about 60 mg, about 75 mg, about 80 mg, about 90 mg, about 95 mg, about 100 mg, about 105 mg, about 110 mg, about 122 mg, about 125 mg, about 150 mg, about 200 mg, about 250 mg, about 300 mg, about 400 mg, about 500 mg, about 600 mg, about 700 mg, about 800 mg, about 900 mg, about 1,000 mg, about 1,200 mg, about 1,500 mg, about 1,750 mg, about 2,000 mg, or any range of doses between any two of those doses.

In some embodiments, the vitamin C present in the compositions of current compositions is ascorbic acid or a salt or an ester thereof. In some embodiments, the vitamin C present in the compositions described herein is selected from the group consisting of sodium ascorbate, calcium ascorbate, potassium ascorbate, magnesium diascorbate, ascorbyl palmitate, and ascorbyl stearate. In some embodiments, the form of vitamin C present in the compositions described herein is an ester of vitamin C, which includes but is not limited to, ascorbyl laurate, ascorbyl myristate, ascorbyl palmitate, ascorbyl stearate, ascorbyl dilaurate, ascorbyl dimyristate, ascorbyl dipalmitate, ascorbyl distearate, ascorbyl trilaurate, ascorbyl trimyristate, ascorbyl tripalmitate, ascorbyl tristearate, ascorbyl tetralaurate, ascorbyl tetramyristate ascorbyl tetrapalmitate, ascorbyl tetrastearate, and mixtures thereof. In the preferred embodiment, the form of vitamin C present in the compositions described herein is an ester of vitamin C, which includes but is not limited to, ascorbyl laurate, ascorbyl myristate, ascorbyl palmitate, ascorbyl stearate, and mixtures thereof.

In some embodiments, the compositions described herein contain about 1 IU to about 200,000 IU of vitamin D. In some embodiments, the amount of vitamin D present in an adult dose of compositions is between from about 100 IU to about 5000 IU. In some embodiments, the amount of vitamin D is from about 400 IU to about 1,200 IU. In some embodiments, the amount of vitamin D is present in an adult dose is from about 100 IU to about 20,000 IU, from 200 IU to 1,500 IU or from 400 IU to 1,200 IU. In some embodiments, the amount of vitamin D is present in a pediatric dose is from about 50 IU to about 200 IU, from 150 IU to 1,500 IU, or from 300 IU to 1,200 IU. In some embodiments, the amount of vitamin D present in an adult dose can be about 1 IU to about 10 IU, about 10 IU to about 100 IU, about 50 IU to about 200 IU, about 100 IU to about 250 IU, about 200 IU to about 600 IU, about 250 IU to about 750 IU, about 300 IU to about 900 IU, about 400 IU to about 1,200 IU, about 500 IU to about 1,500 IU, about 600 IU to about 2,000 IU, about 750 IU to about 2,500 IU, about 800 IU to about 4,000 IU, about 1,000 IU to about 5,000 IU, about 1,500 IU to about 7,500 IU, about 2,000 IU to about 10,000 IU, about 3,000 IU to about 15,000 IU, about 4,000 IU to about 20,000 IU, about 10,000 IU to about 50,000 IU, about 25,000 IU to about 100,000 IU, or about 50,000 IU to about 200,000 IU. In some embodiments, the amount of vitamin D present in an adult dose can be about 1 IU, about 5 IU, about 10 IU, about 25 IU, about 50 IU, about 100 IU, about 200 IU, about 250 IU, about 300 IU, about 400 IU, about 500 IU, about 600 IU, about 700 IU, about 800 IU, about 900 IU, about 1,000 IU, about 1,100 IU, about 1,250 IU, about 1,500 IU, about 1,600 IU, about 1,800 IU, about 2,000 IU, about 2,250 IU, about 2,500 IU, about 2,750 IU, about 3,000 IU, about 3,250

IU, about 3,500 IU, about 3,750 IU, about 4,000 IU, about 4,250 IU, about 4,500 IU, about 4,750 IU, about 5,000 IU, about 5,250 IU, about 5,500 IU, about 5,750 IU, about 6,000 IU, about 7,000 IU, about 8,000 IU, about 9,000 IU, about 10,000 IU, about 12,500 IU, about 15,000 IU, about 20,000 IU, about 30,000 IU, about 40,000 IU, about 50,000 IU, about 75,000 IU, about 80,000 IU, about 100,000 IU, about 125,000 IU, about 150,000 IU, about 175,000 IU, about 200,000 IU or any range of doses between any two of those doses. In some embodiments, the amount of vitamin D present in a pediatric dose can be about 1 IU to about 5 IU, about 5 IU to about 50 IU, about 25 IU to about 100 IU, about 50 IU to about 125 IU, about 100 IU to about 300 IU, about 125 IU to about 400 IU, about 150 IU to about 500 IU, about 200 IU to about 600 IU, about 250 IU to about 700 IU, about 300 IU to about 1000 IU, about 600 IU to about 2000 IU, about 750 IU to about 2500 IU, about 800 IU to about 4000 IU, about 1000 IU to about 5000 IU, about 1500 IU to about 7500 IU, about 2000 IU to about 10000 IU, about 3000 IU to about 15000 IU, about 4000 IU to about 20000 IU, about 10000 IU to about 50000 IU, about 25000 IU to about 100000 IU, or about 50,000 IU to about 200000 IU. In some embodiments, the amount of vitamin D present in a pediatric dose can be about 1 IU, about 5 IU, about 10 IU, about 25 IU, about 50 IU, about 100 IU, about 200 IU, about 250 IU, about 300 IU, about 400 IU, about 500 IU, about 600 IU, about 700 IU, about 800 IU, about 900 IU, about 1,000 IU, about 1,100 IU, about 1,250 IU, about 1,500 IU, about 1,600 IU, about 1,800 IU, about 2,000 IU, about 2,250 IU, about 2,500 IU, about 2,750 IU, about 3,000 IU, about 3,250 IU, about 3,500 IU, about 3,750 IU, about 4,000 IU, about 4,250 IU, about 4,500 IU, about 4,750 IU, about 5,000 IU, about 5,250 IU, about 5,500 IU, about 5,750 IU, about 6,000 IU, about 7,000 IU, about 8,000 IU, about 9,000 IU, about 10,000 IU, about 12,500 IU, about 15,000 IU, about 20,000 IU, about 30,000 IU, about 40,000 IU, about 50,000 IU, about 75,000 IU, about 80,000 IU, about 100,000 IU, about 125,000 IU, about 150,000 IU, about 175,000 IU, about 200,000 IU.

In some embodiments, the vitamin D present in the pharmaceutical compositions of current compositions is in the form vitamin D1, vitamin D2, vitamin D3, vitamin D4, vitamin D5 or a mixture thereof, or a hydroxy derivative thereof. In some embodiments, the vitamin D is 1,25-dihydroxy Vitamin D. In some embodiments, the vitamin D is Vitamin D3, for example, 1,25-dihydroxy Vitamin D3.

In some embodiments, the pharmaceutical compositions described herein contain a formulation comprising one or more non-pathogenic probiotic bacteria. In some embodiments, the probiotic bacteria present in the pharmaceutical composition may comprise about 1 billion to about 500 billion colony forming units (CFU) of one or more probiotic bacteria. In some embodiments, the composition contains from about from about 25 billion to about 51 billion colony forming units (CFU) of one or more probiotic bacteria. In some embodiments, the amount of each of the one or more probiotic bacteria is present in an adult dose is from about 5 billion to about 100 billion CFU, from about 10 billion to about 80 billion CFU or from about 25 billion to about 51 billion CFU. In some embodiments, the amount of each of the one or more probiotic bacteria is present in a pediatric dose is from about 2 billion to about 100 billion CFU, from about 5 billion to about 50 billion CFU, or from about 10 billion to about 30 billion CFU. In some embodiments, the amount of each of the one or more probiotic bacteria is present in a dose of about 1 billion CFU, about 2 billion CFU, about 3 billion CFU, about 4 billion CFU, about 5 billion CFU, about 6 billion CFU, about 7 billion CFU, about 8 billion CFU, about 9 billion CFU, about 10 billion CFU, about 11 billion CFU, about 12 billion CFU, about 13 billion CFU, about 14 billion CFU, about 15 billion CFU, about 16 billion CFU, about 17 billion CFU, about 18 billion CFU, about 19 billion CFU, about 20 billion CFU, about 21 billion CFU, about 22 billion CFU, about 23 billion CFU, about 24 billion CFU, about 25 billion CFU billion CFU, about 26 billion CFU, about 27 billion CFU, about 28 billion CFU, about 29 billion CFU, about 30 billion CFU, about 31 billion CFU, about 32 billion CFU, about 33 billion CFU, about 34 billion CFU, about 35 billion CFU, about 36 billion CFU, about 37 billion CFU, about 38 billion CFU, about 39 billion CFU, about 40 billion CFU, about 41 billion CFU, about 42 billion CFU, about 43 billion CFU, about 44 billion CFU, about 45 billion CFU, about 46 billion CFU, about 47 billion CFU, about 48 billion CFU, about 49 billion CFU, about 50 billion CFU, about 51 billion CFU, about 52 billion CFU, about 53 billion CFU, about 54 billion CFU, about 55 billion CFU, about 56 billion CFU, about 57 billion CFU, about 58 billion CFU, about 59 billion CFU, about 60 billion CFU, about 61 billion CFU, about 62 billion CFU, about 63 billion CFU, about 64 billion CFU, about 65 billion CFU, about 66 billion CFU, about, 67 billion CFU, about, 68 billion CFU, about 69 billion CFU, about 70 billion CFU, about 71 billion CFU, about 72 billion CFU, about 73 billion CFU, about 74 billion CFU, about 75 billion CFU, about 76 billion CFU, about 77 billion CFU, about 78 billion CFU, about 79 billion CFU, about 80 billion CFU, about 81 billion CFU, about, 82 billion CFU, about, 83 billion CFU, about 84 billion CFU, about 85 billion CFU, about 86 billion CFU, about 87 billion CFU, about, 88 billion CFU, about 89 billion CFU, about 90 billion CFU, about 91 billion CFU, about 92 billion CFU, about 93 billion CFU, about 94 billion CFU, about 95 billion CFU, about 96 billion CFU, about 97 billion CFU, about 98 billion CFU, about 99 billion CFU, about 100 billion CFU, about 105 billion CFU, about 110 billion CFU, about, 115 billion CFU, about 120 billion CFU, about 125 billion CFU, about 130 billion CFU, about 140 billion CFU, about 150 billion CFU, about 160 billion CFU, about 170 billion CFU, about 175 billion CFU, about, 180 billion CFU, about 190 billion CFU, about 200, 210 billion CFU, about 220 billion CFU, about 225 billion CFU, about 230 billion CFU, about 240 billion CFU, about 250 billion CFU, about 260 billion CFU, about 270 billion CFU, about 275 billion CFU, about 280 billion CFU, about 290 billion CFU, about 300 billion CFU, about 310 billion CFU, about 320 billion CFU, about 325 billion CFU, about 330 billion CFU, about 340 billion CFU, about 350 billion CFU, about 360 billion CFU, about 370 billion CFU, about 375 billion CFU, about 380 billion CFU, about, 390 billion CFU, about 400, 410 billion CFU, about 420 billion CFU, about 430 billion CFU, about 440 billion CFU, about 450 billion CFU, about 460 billion CFU, about 470 billion CFU, about 480 billion CFU, about 490 billion CFU, or about 500 billion CFU, or any range of CFU between any two of the recited CFU amounts.

In some embodiments, the compositions and probiotic formulations described herein comprises one or more probiotic bacteria selected from the group consisting of *Lactobacillus, Bifidobacterium, Strepetococcus, Pediococcus, Oenococcus, Leuconostoc, Saccharomyces, Enterococcus, Bacillus, Escherichia coli*. In some embodiments, the composition comprises one or more probiotic bacteria selected from the group consisting of *Bifidobacterium lactis, Lactobaccillus acidophilu, Bifidobacterium breve, Bifidobacterium longum, Lactobacillus casei, Lactobacillus plantarum*,

*Lactobacillus arginine, Lactobacillus paracasei, Lactobacillus rhamnosus, Lactobacillus bulgaricus, Saccharomyces boulardii*, and *E. coli* Nissle 1917. In some embodiments, the composition comprises about 25 billion CFU of *Bifidobacterium lactis*, about *Lactobaccillus acidophilus* 15 billion CFU, about 2.5 billion CFU of *Bifidobacterium breve*, about 2.5 billion CFU of *Bifidobacterium longum*, about 1.50 billion CFU of *Lactobacillus casei*, about 1 billion CFU of *Lactobacillus plantarum*, about 1 billion CFU of *Lactobacillus arginine*, about 1 billion CFU of *Lactobacillus paracasei*, about 500 million CFU of *Lactobacillus rhamnosus* and about 500 million CFU of *Lactobacillus bulgaricus*.

In some embodiments, the composition is administered one to eight times a day. In some embodiments, the composition is administered once, twice, thrice, or four times a day.

In some embodiments, the composition is formulated as a unit dose formulation. In some embodiments, the composition the composition is formulated as a tablet, capsule, troches, lozenges, pellets, liquid, serum, yogurt, tea, drink, drops or aerosol, or a combination thereof. In some embodiments, the composition is enterically coated.

In some embodiments the subject to whom the treatment is administered may include or exclude individuals under physical stress, such as marathon runners, skiers, or soldiers in subarctic environments.

In some embodiments, the composition further comprises one or more agents selected from a prebiotic, a herbal extract, an antibiotic, a decongestant, an antihistamine, an analgesic, a cough suppressant, an expectorant, mineral, and a further vitamin. In some embodiments, the composition comprises one or more solvents, diluents, or other liquid vehicle, dispersion or suspension aids, surface active agents, isotonic agents, thickening or emulsifying agents, preservatives, solid binders, lubricants or mixtures thereof. In some embodiments, the composition described herein further comprises a binder, a humectant, a disintegrating agent, an absorption accelerator, a wetting agent, an absorbent or a lubricant.

In one aspect, this application describes use of a composition in the preparation of a medicament for preventing, treating, reducing the duration, or reducing the severity of symptoms of the common cold, wherein the composition comprises a formulation of non-pathogenic probiotic bacteria, a vitamin C and a vitamin D. In one aspect, this application features administering a therapeutically effective amount of a composition described herein.

In some embodiments, the compositions described herein include ingredients that are freeze dried (lyophilized). In some embodiments, the compositions described herein include ingredients that are milled and micronized. In some embodiments, the compositions described herein or the ingredients of the formulation are subjected to the processes including, but not limited to, milling, micronization, homogenization, microfluidization, cryogenic spraying process, spray freezing into liquid, lyophilization, lipid-based solubilization, solid dispersion techniques such as spray drying or hot-melt extrusion, and compression. In some embodiments, the compositions described herein are freeze dried (lyophilized) prior to formulating in suitable dosage forms. In some embodiments, the compositions described herein are milled and micronized prior to formulating in suitable dosage forms.

In one aspect, this invention provides a method of preventing, treating, reducing the duration, or reducing the severity of symptoms of the common cold, comprising administration of a pharmaceutical composition comprising a formulation of non-pathogenic probiotic bacteria, a vitamin C and a vitamin D and at least one pharmaceutically acceptable excipient or filler.

In some embodiments, the disclosed pharmaceutical compositions can also include one or more pharmaceutically acceptable excipients, which, as used herein, includes solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, 18th Edition, Part 8 discloses various carriers used in formulating pharmaceutical compositions and known techniques for the preparation thereof. Pharmaceutically acceptable excipients, as used herein, excludes water which has not been sterilized, Except insofar as any conventional carrier medium is incompatible with the selected active agents, such as by producing any undesirable biological effect or otherwise interacting in a deleterious manner with any other component(s) of the pharmaceutical composition, it can be used in the present compositions.

Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose; ethyl cellulose and cellulose acetate; powdered tragacanth; malt; gelatin; talc; excipients such as cocoa butter and suppository waxes; oils such as peanut oil; cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents and preservatives.

In some embodiments, a method of preventing, treating, reducing the duration, or reducing the severity of symptoms of the common cold, described herein comprises administration of the pharmaceutical composition described herein by at least one of the following routes: orally into the digestive tract; orally buccal, sublingual or sublabial; orally by inhalation into the respiratory tract; ocularly, nasally, through the urogenital tract intravesicularly or intravaginally; rectally, dermally, or by injection into the skin, muscle tissue, or organs. In one embodiment, the method of administering is oral. In one embodiment, the method of administering is topical. In one embodiment, the method of administering is through a transdermal patch.

In some embodiments, the disclosed pharmaceutical compositions can be administered by any route of administration including orally into the digestive tract as by swallowing a tablet; orally buccal, sublingual or sublabial as by disintegrating tablet or chewing gum or an oral spray; orally by inhalation into the respiratory tract; ocular or nasal as by drops, ointments or hydrogels, through the urogenital tract intravesicularly or intravaginally, rectally, dermally as by ointments or transdermal patches, or by injection into the skin, muscle tissue, or organs as appropriate. In some embodiments, oral administration is preferred. In some embodiments, certain administration methods, include the step of administering the pharmaceutical composition orally one or more times a day, to obtain the desired therapeutic effect.

In some embodiments, liquid dosage forms for oral administration are contemplated and pharmaceutically acceptable emulsions, microemulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In some embodiments, besides inert diluents, the oral compositions can also include adjuvants such as wetting agents, emulsifying and suspending agents, sweetening, flavoring, and perfuming agents. In some embodiments, conventional nutraceutical procedures can be employed to create liquid drinks, powder mixes or food-stuffs comprising the ingredients.

Pharmaceutical compositions for rectal or vaginal administration are preferably suppositories which can be prepared by mixing the selected active agents with suitable non-irritating excipients or carriers such as cocoa butter, polyethylene glycol or a suppository wax which are solid at ambient temperature but liquid at body temperature and therefore melt in the rectum or vaginal cavity to release the active agent.

In some embodiments, dosage forms such as dragees, pills, granules, pastes, suspensions, liquids, solutions, suspensions, emulsions, elixirs, syrups, drops, powders, electuaries, capsules, tablets, lozenges, pastilles, gels, pastes, ointments, creams, lotions, oils, foams, sprays, mists, or aerosols are contemplated.

In some embodiments, the disclosed pharmaceutical compositions are particularly useful when incorporated into tablets or capsules. In some embodiments, the disclosed compositions are particularly useful when incorporated compressed tablet which is prepared by a method comprising compressing in a suitable machine, the composition in a free flowing form such as powder or granules, optionally mixed with a binder, lubricant, inert diluent, surface active or dispersing agent. In some embodiments, the compressed tablets is prepared by intermediate compaction of the powder or granules comprising the current formulations before the final compression into tablet forms, optionally following addition of further excipients described herein to the compacted blend before compression. In some embodiments, the compressed tablets described herein are further coated with a coating agent to form film coated tablets or shells of agents such as such as enteric coatings, release controlling coatings, film coating. The coating agent may be suspended in a solution or directly taken from a commercially available coating solution which is sprayed onto the compressed pellets. Preferably, all process steps are carried out in controlled atmosphere, such as low moisture, oxygen, temperature and light protection.

In some embodiments, the active agents can be mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In some embodiments, the dosage form may also comprise buffering agents.

Tablets can be formed by mixing the ingredients with a binder which is used to impart cohesive qualities to a tablet formulation, and thus ensure that the tablet remains intact after compaction. Suitable binders include, but are not limited to, starches such as pregelatinized maize starch, alginates, gelatin, carboxymethylcellulose, sugars (for example, sucrose, glucose, dextrose, and maltodextrin), waxes, natural and synthetic gums, polyvinylpyrrolidone (PVP), and cellulosic polymers (for example, microcrystalline cellulose, hydroxypropyl cellulose, hydroxypropyl methylcellulose, methyl cellulose, and hydroxyethyl cellulose).

Under certain circumstances there is a requirement for fast disintegrating or dissolving tablets which can be administered even without water. Such fast dissolving tablets disperse readily to form a suspension or solution of the active agents after mixing with the saliva, which is easily swallowed by the patients. These are particularly suitable for children or aged patients who have difficulty in chewing and/or swallowing an intact tablet/capsule. Fast mouth dissolving tablets are also suitable for patients suffering from nausea or vomiting; who have an upper gastrointestinal tract disease e.g., injury in food pipe; who have undergone upper GI surgery; who are prostrate; who are elderly and have frequent urination problems at night; who are incapacitated elderly patients e.g. suffering from Parkinson's disease, who are in a situation where water is not available.

Fast dissolving tablets can be formed from the active agents which can be admixed with at least one water soluble sugar in an amount of from 5 to 95 weight % of the total dosage form and at least one non-sugar sweetener in a fast release form in an amount of from 0 to 10 weight % of the total dosage form; and at least one non-sugar sweetener in a mucoadhesive slow release form in an amount of from 0.5 to 20 weight % of the total dosage form. The mixture can then be compressed into a tablet or other solid dosage form using known methods.

The active agents can also be in an encapsulated or microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agents may be admixed with at least one inert diluent such as sucrose, lactose or starch. Such dosage forms may also comprise additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner.

In some embodiments, the active agents can be incorporated into liposomes by any known method and the liposomes can then be encapsulated in bead form. The beads can be formed by suspending the liposomes in a physical and potentially physiochemical bonding solution. The bonding solution can contain at least one organic compound such as agarose, cellulose, sodium alginate, chitosans, polymeric substances or other compounds with the necessary characteristic of physical or physiochemical bonding. This solution can then be introduced into a second solution containing from about 1 to 2% by weight of an inorganic salt. The effect of the interaction of the solutions is to harden the outer most exposed areas of the introduced liposome solution. The inorganic salt can be calcium chloride or sodium hydroxide, although other types of inorganic salts can be used such as calcium sulfate, calcium carbonate, magnesium chloride, magnesium sulfate, barium chloride, barium sulfate and the like.

Dosage forms for topical or transdermal administration of the active agents include ointments, pastes, creams, lotions, gels, powders, solutions, sprays, inhalants or transdermal patches. Additionally, the use of transdermal patches as are known. Transdermal patches have the added advantage of providing controlled delivery of active agents to the body. Such dosage forms can be made by dissolving or dispensing the active agents in a suitable medium as is known. Absorption enhancers can also be used to increase the flux of the active agents across the skin. The rate can be controlled by either providing a rate controlling membrane or by dispersing the active agents in a polymer matrix or gel. Eardrops and eye drops are also contemplated.

In some embodiments, the pharmaceutical compositions can be formulated in immediate release, sustained release, or delayed release formulations.

A sustained-release form is a form suitable for providing controlled-release of the ingredients in an aqueous medium over a sustained period of time (e.g., 8 hours, 12 hours, 24 hours). This provides for an increased duration of the ingredients allowing once-daily dosing. Such compositions can include a release-retarding material in the form of, for example, a matrix or a coating.

In some embodiments, release-retarding materials are be used. These include for example acrylic polymers, alkylcelluloses, shellac, zein, waxes, hydrogenated vegetable oil, hydrogenated castor oil as are known and their combinations. The oral dosage form can contain from about 1 wt. % to about 80 wt. % of the release-retarding material. Suitable acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. Suitable acrylic polymers include methacrylate copolymers as fully polymerized copolymers of acrylic and methacrylic acid esters with a low content of quaternary ammonium groups. Suitable alkylcelluloses include, for example, ethylcellulose. Those skilled in the art will appreciate that other cellulosic polymers, including other alkyl cellulosic polymers, can be substituted for part or all of the ethylcellulose.

The release-retarding material can also include other additives such as an erosion-promoting agent (e.g., starch and gums); and/or a semi-permeable polymer. In addition to the above ingredients, a sustained-release dosage form can also contain suitable quantities of other materials, e.g., diluents, lubricants, binders, granulating aids, colorants, flavorants and glidants that are conventional in the pharmaceutical art. The release-retarding material optionally includes an exit means comprising at least one passageway, orifice, or the like. The passageway can have a suitable shape, such as round, triangular, square, elliptical, irregular, etc.

In some embodiments, sustained release pharmaceutical compositions can be incorporated into a dosage form that is mechanically stabilized to increase the difficulty of comminuting by conventional methods, such as pounding, crushing, grinding in a mortar etc. In such dosage forms the active agents can still release under physiological conditions with the intended delayed release profile. This can be helpful in maintaining the release profile of sustained release formulations when comminution would otherwise compromise the release characteristics by partially destroying the matrix controlling release and/or the film coating on the dosage form which controls release. Stabile dosage forms can be obtained by including a polymer polyalkylene oxide having a weight average molecular weight or viscosity average molecular weight of at least $0.5 \times 10^6$ g/mol in combination with at least one further polymer, preferably also having a weight average molecular weight (Mw) or viscosity average molecular weight of at least $0.5 \times 10^6$ g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyimide, polylactide, polyacetal, polylactide/glycolide, polylactone, polyglycolide, polyorthoester, polyanhydride, block polymers of polyethylene glycol and polybutylene terephthalate, polyanhydride and copolymers thereof. The polymers preferably have a viscosity at 25° C. of 4,500 to 17,600 cP, measured in a 5 wt. % aqueous solution, of 400 to 4,000 cP, or of 1,650 to 10,000 cP, measured on a 1 wt. % aqueous solution. In general, the process for the production of the dosage form involves mixing the active agents with the polymer mixture and applying heat and/or force to the mixture to harden the mixture. The heat supplied should preferably not be sufficient to reduce the activity of the active agents. The mixture can be shaped as it hardens. Heat may be supplied directly or with the assistance of ultrasound. Force may be applied and/or the dosage form may be shaped for example by direct tabletting or with the assistance of a suitable extruder, particularly by means of a screw extruder equipped with two screws (twin-screw-extruder) or by means of a planetary gear extruder.

It will also be appreciated that the disclosed active agents and pharmaceutical compositions can be employed in combination therapies, that is, the active agents and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved.

One representative formulation and its use for preventing, treating, reducing the duration, or reducing the severity of symptoms of the common cold, is set forth in the following example.

Example 1

A healthy adult volunteer subject (test subject) was orally administered the following formulation once every day with food for two years (test period): Formula 1: (1) 500 mg as Ester-C®, (2) 1,000 IU of 1,25-dihydroxy Vitamin D, and (3) a probiotic blend of the following bacteria: about 25 billion CFU of *Bifidobacterium lactis*, about 15 billion CFU of *Lactobaccillus acidophilus* about 2.5 billion CFU of *Bifidobacterium breve*, about 2.5 billion CFU of *Bifidobacterium longum*, about 1.50 billion CFU of *Lactobacillus casei*, about 1 billion CFU of *Lactobacillus plantarum*, about 1 billion CFU of *Lactobacillus arginine*, about 1 billion CFU of *Lactobacillus paracasei*, about 500 million CFU of *Lactobacillus rhamnosus*, about 500 million CFU of *Lactobacillus bulgaricus*. Prior to administration of the formulation the adult subject contracted an average of four colds a year. Eight healthy volunteer subjects (control subjects) who were not administered the above formulation each had approximately 5-6 colds over this period of time. The adult volunteer's family members including 2 small children who also had 8-10 colds over the two year period. Whereas the controls (coworkers and family members) contracted common colds several times during the two year test period, the test subject did not contract a common cold even once. Finally in the Winter after the two year study period, the test subject's wife began to develop typical URI prodromal symptoms including a sore throat, stuffy noise, and malaise. She began taking the study formulation twice a day (for one day) and within 24 hours noticed a complete disappearance of the URI symptoms. She then discontinued the study formulation after two doses and again noted the prompt return of her URI symptoms within 24 hours. She then completed a seven day course of twice daily study formulation with complete resolution of her URI symptoms and no further recurrence. The healthy volunteer to whom the formulation was administered is a board certified medical doctor with experience as a clinical research investigator.

Exemplary Formulations

The composition of another exemplary formulation of this disclosure for use in the methods of this disclosure is shown below.

| Formula 2 | |
|---|---|
| Ingredient | Dose |
| 1) Probiotic Blend | 51.5 Billion CFU |
| *Bifidobacterium Lactis* | 25 billion CFU |
| *Lactobaccillus Acidophilus* | 15 billion CFU |
| *Bifidobacterium Breve* | 2.5 billion CFU |
| *Bifidobacterium Longum* | 2.5 billion |
| *Lactobacillus Casei* | 1.50 billion CFU |
| *Lactobacillus Plantarum* | 1 billion CFU |
| *Lactobacillus Arginine* | 1 billion CFU |
| *Lactobacillus Paracasei* | 1 billion CFU |
| *Lactobacillus Rhamnosus* | 1 billion CFU |
| *Lactobacillus Bulgaricus* | 1 Billion CFU |
| 2) Vitamin D3 | 1050 I.U. |
| 3) Vitamin C (Ester-C ®, Calcium Ascorbate) | 500 mg |
| 4) Calcium | 62 mg (as Calcium ascorbate) |
| 5) Citrus Bioflavonoids | 25 mg |
| 6) Acerola | 10 mg |
| 7) Rose Hips | 10 mg |
| 8) Rutin | 5 mg |

The ingredients or amounts of each ingredient may be varied as described in this disclosure. For example, as disclosed herein, the vitamin C component may Ester-C®, which comprises calcium ascorbate and calcium threonate, in any amount disclosed herein. In some embodiments, the vitamin C component may be Ester-C®, which comprises calcium ascorbate and calcium threonate. The vitamin C component may also comprise calcium palmitate and calcium threonate.

In some embodiments, in a pediatric dose the amount of vitamin C may be reduced to 75-100 mg, for example, 75-100 mg of Ester-C®, or any value or range falling within 75-100 mg of vitamin C or Ester-C®. In some embodiments, the formulation excludes vitamin C in the form of ascorbic acid. In some embodiments, the pediatric dose may contain 5-10 billion CFU daily, and each of the components of the probiotic component may be reduced proportionately, e.g., a pediatric formulation may comprise $\frac{1}{10}$ to $\frac{1}{5}$ of the amounts or ranges of amounts of each bacteria disclosed herein.

In some embodiments the formulations comprise 7 strains of lactobacilli and 3 strains of *Bifidobacterium*, non-limiting examples of which are set forth herein.

As another example, in some embodiments, the probiotic component in adult formulations comprises:

| Formula 3 | |
|---|---|
| *Bifidobacterium Lactis* | 25 billion CFU |
| *Lactobaccillus Acidophilus* | 15 billion CFU |
| *Bifidobacterium Breve* | 2.5 billion CFU |
| *Bifidobacterium Longum* | 2.5 billion CFU |
| *Lactobacillus Casei* | 1.50 billion CFU |
| *Lactobacillus Plantarum* | 1 billion CFU |
| *Lactobacillus Arginine* | 1 billion CFU |
| *Lactobacillus Paracasei* | 1 billion CFU |
| *Lactobacillus Rhamnosus* | 500 million |
| CFU *Lactobacillus Bulgaricus* | 500 million CFU |

In pediatric formulations, the amounts of each bacterium may be reduced, e.g., by $\frac{1}{10}$ to $\frac{1}{5}$ the amount in the adult formulation.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

We claim:

1. A method of treating, reducing the duration, or reducing the severity of symptoms of the common cold, comprising administration to a subject in need thereof a therapeutically effective amount of a pharmaceutical composition comprising:
   (a) a formulation of probiotic non-pathogenic bacteria;
   (b) vitamin C wherein the vitamin C is a mixture of calcium ascorbate and calcium threonate; and
   (c) vitamin D.

2. The method of claim 1, wherein the pharmaceutical composition is formulated to be delivered by oral, inhaled or intranasal administration.

3. The method of claim 1, wherein the pharmaceutical composition contains about 1 mg to about 2000 mg of Vitamin C, wherein the Vitamin C is a mixture of calcium ascorbate and calcium threonate.

4. The method of claim 3, wherein the pharmaceutical composition comprises between 250-500 mg of Vitamin C, wherein the Vitamin C is a mixture of calcium ascorbate and calcium threonate.

5. The method of claim 1, wherein the pharmaceutical composition comprises from about 1 IU to about 200,000 IU of Vitamin D.

6. The method of claim 5, wherein the pharmaceutical composition comprises from about 400 IU to about 1200 IU Vitamin D.

7. The method of claim 6, wherein the Vitamin D is in the form Vitamin D1, Vitamin D2, Vitamin D3, Vitamin D4, Vitamin D5 or a mixture thereof, or a hydroxy derivative thereof.

8. The method of claim 6, wherein the Vitamin D is in the form 1,25-dihydroxy Vitamin D2 or 1,25-dihydroxy Vitamin D3.

9. The method of claim 1, wherein the formulation comprises from about 1 billion to about 500 billion colony forming units (CFU) of probiotic bacteria.

10. The method of claim 1, wherein the formulation comprises from about 25 billion to about 51 billion colony forming units (CFU) of probiotic bacteria.

11. The method of claim 1, wherein the formulation comprises one or more probiotic bacterial genera selected from the group consisting of *Lactobacillus, Bifidobacterium, Strepetococcus, Pediococcus, Oenococcus, Leuconostoc, Saccharomyces, Enterococcus, Bacillus*, and *Escherichia coli*.

12. The method of claim 11, wherein the formulation comprises one or more probiotic bacteria selected from the group consisting of *Bifidobacterium lactis, Lactobacillus acidophilus, Bifidobacterium breve, Bifidobacterium longum, Lactobacillus casei, Lactobacillus plantarum, Lactobacillus paracasei, Lactobacillus rhamnosus* and *Lactobacillus bulgaricus*.

13. The method of claim 12, wherein the one or more probiotic bacteria are present at about 25 billion CFU of *Bifidobacterium lactis*, about 15 billion CFU of *Lactobacillus acidophilus*, about 2.5 billion CFU of *Bifidobacterium breve*, about 2.5 billion CFU of *Bifidobacterium longum*, about 1.50 billion CFU of *Lactobacillus casei*, about 1 billion CFU of *Lactobacillus plantarum*, about 1 billion CFU of *Lactobacillus paracasei*, about 500 million CFU of *Lactobacillus rhamnosus* and about 500 million CFU of *Lactobacillus bulgaricus*.

14. The method of claim 1, wherein the pharmaceutical composition is administered one to four times a day.

15. The method of claim 1, wherein the pharmaceutical composition is formulated as a unit dose formulation.

16. The method of claim 1, wherein the pharmaceutical composition is formulated as a tablet, capsule, troches, lozenges, pellets, liquid, syrup, drops or aerosol.

17. The method of claim 16, wherein the pharmaceutical composition is a tablet, capsule, troche, lozenge, or pellet, and said pharmaceutical composition is enterically coated.

18. The method of claim 1, wherein the pharmaceutical composition further comprises a prebiotic.

19. The method of any one of claim 1, wherein the Vitamin D is Vitamin D3.

20. A method of treating, reducing the duration, or reducing the severity of symptoms of the common cold, comprising administration to a subject in need thereof a therapeutically effective amount of a composition wherein the composition comprises
  (a) between 250-500 mg of vitamin C, wherein the vitamin C is a mixture of calcium ascorbate and calcium theronate,
  (b) between 400-1200 IU of vitamin D, and
  (c) from about 25-51 billion colony forming units (CFU) of probiotic bacteria selected from the group consisting of *Bifidobacterium lactis, Lactobacillus acidophilus, Bifidobacterium breve, Bifidobacterium longum, Lactobacillus casei, Lactobacillus plantarum, Lactobacillus paracasei, Lactobacillus rhamnosus* and *Lactobacillus bulgaricus*.

\* \* \* \* \*